US006110661A

United States Patent [19]
Lajoie et al.

[11] Patent Number: 6,110,661
[45] Date of Patent: Aug. 29, 2000

[54] BIOLUMINESCENT REPORTER BACTERIUM

[75] Inventors: Curtis A. Lajoie, Rockwood; Christine Jo Kelly, Philadelphia; Alice C. Layton, Knoxville; Gary S. Sayler, Blain, all of Tenn.

[73] Assignee: Eastman Chemical Company, Kingsport, Tenn.

[21] Appl. No.: 08/944,934

[22] Filed: Oct. 2, 1997

Related U.S. Application Data

[60] Provisional application No. 60/045,248, May 1, 1997.

[51] Int. Cl.[7] .............................. C12Q 1/00; C12Q 1/66; C12Q 1/02
[52] U.S. Cl. .................................. 435/4; 435/8; 435/29; 435/30; 435/69.1; 435/252.3; 435/252.34; 435/252.33; 435/252.31
[58] Field of Search ............................. 435/252.3, 252.34, 435/252.33, 252.31, 4, 8, 29, 30, 69.1

[56] References Cited

U.S. PATENT DOCUMENTS 4,563,331  1/1986  Losee et al. ............................... 422/52

FOREIGN PATENT DOCUMENTS

| 0705904A1 | 8/1995 | European Pat. Off. . |
| WO 90/04037 | 4/1990 | WIPO . |
| WO 93/05142 | 3/1993 | WIPO . |
| WO 96/30760 | 10/1996 | WIPO . |

OTHER PUBLICATIONS

Palomares et al. "Firefly luciferase as a reporter enzyme for measuring gene expression in vegetative and symbiotic Rhizobium meliloti and other gram–negative bacteria." Gene. Sep. 1, 1989; 81(1): 55–64.

Flemming et al "Survival of lux–lac–marked biosurfactant–producing *Pseudomonas aeruginosa* UG2L in soil monitored by nonselective plating and PCR." Appl Environ Microbiol. May 1, 1994: 60(5): 1606–1613.

Paton "Use of Luminescence–Marked Bacteria to Assess CopperBioavailability in Malt Whiskey Distillery Effluent" Chemosphere vol. 31, No. 5, p. 3217(8) Sep. 1, 1995.

Fernandez,A., et al., "Assessment of Toxicity of River Water and Effluents by the Bioluminescence Assay Using *Photobacterium Phosphoreum*"; *Water Research,* vol. 29, No. 5, May 1995, pp. 1281–1286.

Chemical Abstracts, vol. 119, No. 10, 1993, Arquiaga M.C. et al., "Microbiology of high–sodium–nitrite wastewater treatment", p. 462; col. 1; *Environmental Pollut.*; vol. 81, No. 1, 1993, pp. 1–6.

Chemical Abstracts, vol. 95, No. 10, 1981, Zeana R. et al., "Activated sludge metabolism guidance to stimulate its catabolic activity", p. 291; col. 1; *Stud. Epurarea Apelor;* vol. 19, 1979, pp. 16–28.

Fesefeldt, A. and Gliesche, C.G. "Identification of Hyphomicrobium spp. using PCR–Amplified Fragments of the mxaF as a Molecular Marker" *System. Appl. Microbiol.* 20:387–396, 1997.

Ming–Chien, S., Cha, Daniel K., and Anderson, P.R. "Influence of Selector Technology on Heavy Metal Removal of Activated Sludge Secondary Effects of Selector Technology" *Wat. Res.* 29(3):971–976, 1995.

Myers, A.J. and Myers, C.D. Hyphomicrobium–mediated Sludge Bulding in and Industrial Wastewatewater Treatment System Abstract 86th Annual Meeting of the Amer. Society for Microbiol., Washington, DC Mar. 23–28, 1986, Abstracts of the Annual Meeting—1986,No. N–93, p. 257.

Kong et al. (1996) "Simultaneous determination of inhibition kinetics of carbon oxidation and nitrification with a respirometer." *Water Res.,* 30(4),825.

Kilroy and Gray (1992) "The toxicity of four organic solvents commonly used in the pharmaceutical industry to activated sludge." *Water Res.,* 26(7), 887.

Strotmann and Eglsaer (1994) "The toxicity of substituted phenols in the nitrification inhibition test and luminescent bacteria test," *Ecotoxicol Environ. Saf.,* 30, 269.

Volskay and Grady (1988) "Toxicity of selected RCRA compounds to activated sludge microorganisms." *J. Water Pollut. Control Fed.,* 60(10), 1850.

Dutka et al. (1983) "Comparison of several microbiological toxicity screening tests." *Water Res.,* 17(10), 1363.

Paton et al. (1995) "Use of luminescence–marked bacteria to assess copper bioavailability in malt whisky distillery effluent." *Chemosphere,* 31(5), 3217.

*Primary Examiner*—Ponnathapura Achutamurthy
*Assistant Examiner*—Bradley S. Mayhew
*Attorney, Agent, or Firm*—Cheryl J. Tubach; Harry J. Gwinnell

[57] ABSTRACT

The present invention provides a reporter bacterium, comprising a bacterium that occurs naturally in a biological sludge and that contains a nucleic acid that encodes a reporter protein not found in the naturally occurring bacterium. The nucleic acid can encode a bioluminescent reporter protein. A method and apparatus are also provided for detecting the presence of toxicity in a wastewater treatment influent stream, comprising contacting the influent with a reporter bacterium of the present invention; monitoring the expression of the reporter protein by the reporter bacterium; and correlating a reduction in the expression of the reporter protein with the presence of toxicity. In an additional embodiment, the present invention provides a method and apparatus for determining the effect of a known dose of an oxidative phosphorylation decoupling agent on biological wastewater sludge, comprising contacting a sample of the sludge containing a known dose of the decoupling agent and a control sample, with a reporter bacterium of the present invention; comparing the signal output by the reporter bacteria in the sludge sample containing the decoupling agent with the signal output by the reporter bacteria in the sludge sample not containing the decoupling agent; and correlating a decrease in signal output in the decoupled sample as compared to the signal output in the control sample with an action of the decoupling agent, whereby the effect of the known dose of the decoupling agent is determined.

6 Claims, 7 Drawing Sheets

BIOLUMINESCENT REPORTER BACTERIUM

The present application claims priority of U.S. provisional application Ser. No. 60/045,248, filed May 1, 1997.

BACKGROUND OF THE INVENTION

1. Field of the Invention

The present invention relates to the detection of toxic conditions in biological sludges in biological wastewater treatment systems. More particularly, the invention provides a bioluminescent bacterium for use in detecting toxic conditions in biological wastewater treatment systems.

2. Background Art

The problem of pinfloc formation in wastewater solids can be caused by toxic shock, starvation [caused by high mean cell residence time (MCRT), variable organic loads or influent flow patterns], and/or pump shear (Jenkins, et al., 1993). The transient nature of toxic shock and influent organic loads often renders elucidation of the causative factor difficult. Toxicity of influent wastewater to wastewater solids treatment microbial communities can result in higher operating costs and reduced effluent water quality (Jenkins et al., 1993). Toxic shock causes death of microorganisms and loss of floc structure. The resulting small flocs (pin flocs) settle poorly in downstream clarifiers, and costly polymer addition may be required to meet effluent water quality standards. Effluent violations may result from release of toxicants to receiving waters as a result of loss of specific chemical degrading populations. These effects can be avoided if the incoming waste stream is screened for toxicity, and protective action taken. For example, the toxic stream can be diverted to a temporary holding basin and returned to the waste treatment system at a slower rate to avoid high toxicant concentrations that may otherwise seriously impact wastewater solids quality.

An ideal assessment method for wastewater toxicity is inexpensive, on-line, easy to use, sensitive and relevant to wastewater solids microbial communities. The existing methods of assessing toxicity include: (1) chemical analysis; (2) microscopic analysis; (3) respirometric inhibition methods; and (4) bioluminescence (Kilroy and Gray, 1992).

Chemical analysis of influent wastewater for toxicants requires knowledge of the identity of potential toxicants, is expensive (aton, et al., 1995) and is not rapid enough for effective process control responses. The time available for diversion of toxic influents to holding basins is often on the order of seconds to minutes. Chemical analysis of municipal treatment plant influents is especially problematic due to the complexity and uncertainty of the potential influent toxicants. Microscopic methods for evaluating toxic events are also time consuming because flocs must be examined microscopically. In addition, pin flocs commonly indicative of toxic shock can be caused by other environmental or operating conditions (Jenkins et al., 1993). Microscopic examination of changes in microbial populations or morphology can identify toxic shock, but cannot be used as a preventative method for control of incoming toxic waste streams.

The most common method for assessing wastewater toxicity to wastewater solids is respirometric inhibition (Kong et al., 1996; Strotmann and Eglsaer, 1994). The oxygen consumption rate of the wastewater solids with a wastewater sample is compared to the consumption rate with a non-toxic control. The $EC_{50}$ toxicity value is the effective concentration of toxicant for which there is a 50% reduction in oxygen consumption rate (Volskay and Grady, 1988). Decreases in respiration rates indicate toxicity. The respirometry method assesses the metabolic state of the entire community, but is not easily tailored to specific critical populations of potential interest. Determination of toxicity with respirometry can be done on-line, but current technology tends to be expensive and time consuming. In batch grab samples, there is a delay between a toxic compound in the incoming waste stream and the toxicity indication.

The use of bioluminescent microorganisms for toxicity measurements is relatively simple, rapid, does not require chemical identification of the toxic agents and can be used for on-line measurements. Currently available bioluminescent methods to assess ecotoxicity include naturally luminescent marine bacteria, primarily the MICROTOX system (AZUR Environmental), which is considered the benchmark of bioluminescent methods (Paton et al., 1995). This test consists of thawing *Photobacterium phosphoreum* cells and adding them to a saline buffered, neutral pH solution and measuring the bioluminescent response of the bacteria in a wastewater sample as measured with a luminometer (Dutka et al., 1983). For comparison, the $EC_{50}$ value is the concentration of toxicant that results in a 50% reduction in bioluminescence from the baseline level. The inherent difficulties of the MICROTOX system are the requirements for pH and saline buffering, problems with reproducibility (Dutka et al., 1983), its unsuitability for application as an on-line or continuous monitoring system and that the organism is not representative of those species which populate wastewater solids communities.

Another problem of wastewater treatment involves the high cost of disposing of large quantities of sludge. The use of a decoupling agent can reduce sludge volume, but this presents the difficulty of accurately measuring the effect of the decoupling agent on sludge dynamics.

The present invention meets these needs by providing a rapid and effective method for assessing toxicity and for measuring the effect of a decoupling agent in wastewater treatment systems.

SUMMARY OF THE INVENTION

The present invention provides a reporter bacterium, comprising a bacterium that occurs naturally in a biological sludge and that contains a nucleic acid that encodes a reporter protein not found in the naturally occurring bacterium. The nucleic acid can encode a bioluminescent reporter protein, thus providing a bioluminescent reporter bacterium.

Also provided is a bioluminescent reporter bacterium, obtained by the process comprising: contacting a bacteria-containing sample of a biological sludge with a donor bacterium, wherein the donor bacterium contains a nucleic acid that encodes a bioluminescent reporter protein that does not naturally occur in biological sludge bacteria under conditions whereby mating can occur.

Further provided is a bioluminescent reporter bacteriumn, obtained by the process comprising: delivering to an isolated bacterium that occurs naturally in a biological sludge, a nucleic acid construct which contains a nucleic acid that encodes a bioluminescent reporter protein that does not occur naturally in the biological sludge bacterium.

In addition, the present invention provides a method for making a bioluminescent reporter bacterium, comprising: contacting a bacteria-containing sample of a biological sludge with a bacterium that contains a nucleic acid that encodes a bioluminescent reporter protein, and that does not naturally occur in a biological sludge, under conditions whereby the nucleic acid encoding the reporter protein is taken up by bacteria in the sludge sample to generate a bioluminescent reporter bacterium.

Furthermore, the present invention provides a method for making a bioluminescent reporter bacterium, comprising: delivering to an isolated bacterium, that occurs naturally in a biological sludge, a nucleic acid construct which contains a nucleic acid that encodes a bioluminescent reporter protein that does not occur naturally in the bacterium, under conditions whereby the nucleic acid encoding the reporter protein is taken up by the bacterium to generate a bioluminescent reporter bacterium.

A method for detecting the presence of toxicity in a wastewater treatment influent stream is additionally provided, comprising: contacting the influent with a reporter bacterium of the present invention; detecting the expression of the reporter protein by the reporter bacterium; and correlating a reduction in the expression of the reporter protein with the presence of toxicity Furthermore, the present invention provides a method for detecting a toxic condition of a wastewater fluid in a biological wastewater treatment facility having an influent stream of wastewater fluid, comprising: a) contacting the influent with a reporter bacterium that expresses a reporter protein; b) detecting the expression of the reporter protein by the reporter bacterium; and c) correlating a reduction in the expression of the reporter protein with the presence of toxicity.

The present invention also provides a method for determining the effect of a known dose of an oxidative phosphorylation decoupling agent on biological wastewater sludge, comprising: a) contacting a sample of the sludge, containing a known dose of the decoupling agent, with a bioluminescent reporter bacterium of the present invention; b) contacting a sample of the sludge, not containing the decoupling agent, with a bioluminescent reporter bacterium of the present invention; c) detecting light output by the reporter bacterium in the sludge sample containing the decoupling agent; d) detecting light output by the reporter bacterium in the sludge sample not containing the decoupling agent; e) comparing the light output by the reporter bacterium in the sludge sample containing the decoupling agent with the light output by the reporter bacterium in the sludge sample not containing the decoupling agent; and f) correlating a decrease in light output by the reporter bacterium of step (c) as compared to the light output by the reporter bacterium of step (d) with an action of the decoupling agent, whereby the effect of the known dose of the decoupling agent is determined.

In addition, the present invention provides a method for continuously regulating the energetics in biological wastewater sludge, comprising: continuously monitoring the effect of a known dose of a decoupling agent in a wastewater sludge sample according to the methods described herein and continuously increasing or reducing the dose of decoupling agent as needed to maintain a consistent selected output of light by the reporter bacterium.

An apparatus for detecting a toxic condition in a wastewater influent at a biological wastewater treatment facility is provided. The apparatus can comprise: a) a first chamber, containing a reporter bacterium of the present invention; b) means in fluid communication with the first chamber for diverting a portion of the wastewater influent into the first chamber; and c) means in photometric proximity to the first chamber for detecting light output from the reporter bacterium, whereby a reduction in light output detects a toxic condition.

Also provided is an apparatus for monitoring the effect of a decoupling agent on sludge energetics in a biological wastewater treatment facility. The apparatus can comprise: a) a first chamber, containing a reporter bacterium of the present invention for receiving a portion of a biological sludge; b) means in fluid communication with the first chamber for diverting a portion of the biological sludge, to which a decoupling agent has been added, into the first chamber; and c) means in photometric proximity to the first chamber for detecting light output from the reporter bacterium, whereby a reduction in light output correlates with the effect of a decoupling agent on sludge energetics.

DETAILED DESCRIPTION OF THE INVENTION

A reporter bacterium, comprising a bacterium that occurs naturally in a biological sludge and that contains a nucleic acid that encodes a reporter protein not found in the naturally occurring bacterium is provided. The reporter protem produces a detectable signal. As used herein "biological sludge" includes sludges from wastewater treatment facilities (e.g., industrial, municipal, etc.) and is also commonly referred to as biosolids and wastewater solids.

The bacteria of the present invention from which the reporter bacteria of this invention can be produced can be any bacteria which do not naturally contain a bioluminescent reporter gene, and in a preferred embodiment are those bacteria which occur naturally in a biological sludge. Although the invention is not limited to bacteria isolated directly from biological sludge, advantages result from using bacterial strains that are present in biological sludge and still adapted to sludge or, at least, have not been so well adapted to long term culture in a non-sludge environment that they will not grow well in biological sludge. The reporter bacterium can be made using a naturally occurring bacterium isolated from a biological sludge or sample of sludge containing bacteria. An example of the reporter bacterium can be the Shk 1 reporter bacterium, which is produced from a naturally occurring bacterium present in a biological wastewater sludge in the mating method described in the Examples.

Also provided in the present invention is a bioluminescent reporter bacterium, obtained by the process comprising: a) contacting a bacteria-containing sample of biological sludge with a donor bacterium, wherein the donor bacterium contains a nucleic acid that encodes a bioluminescent reporter protein that does not naturally occur in biological sludge bacteria under conditions whereby mating can occur, and b) selecting for a reporter bacterium, originally from the biological sludge sample, that expresses bioluminescence (i.e., bioluminescent reporter bacterium). Likewise, a mixture of bacteria (of known or unknown taxonomy) can be obtained from a sample of biological sludge and contacted with the donor bacterium to produce a reporter bacterium.

This process of mating bacteria from a sample of biological sludge with a donor bacterial strain carrying the reporter protein gene in an expression construct has significant advantages. For example, mating of signal-encoding donor strains directly with wastewater solids bacterial strains is a rapid and effective method of developing treatment plant-specific toxicity biosensors. Recipients of a construct that encodes a bioluminescent reporter protein (bioluminescent reporter bacteria) with high light output can be chosen by visual examination of resulting colonies on agar plates. Using strains that produce easily visible light, it is possible to determine the toxicity of potential influent chemicals or grab samples of influent without the use of light detecting equipment, although light detecting devices are preferred for continuous, on-line monitoring of light output and for detecting quantitative changes in the degree of light emitted. Examples of such light detecting devices can include, but are not limited to, devices which transmit light, such as a liquid light pipe or fiber optic cable, coupled to a device which measures light, such as, for example, a photomultiplier or photodiode.

In the above sludge mating method, the donor bacterium (donor strain) which contains the nucleic acid that encodes the reporter protein can be selected from among the bacteria used as donors in other contexts, for example, *Escheiichia. coli, Alcaligenes eutrophus* and *Pseudomonas puida*, although, theoretically, almost all known bacteria could serve as donors. It is preferable to choose a donor strain for malting the reporter bacterium that can be selected against in the selecting step. For example, the donor bacterium may have a nutritional requirement that is different from the nutritional needs of the sludge bacteria, and thus, will not be expected to thrive in sludge. Thus, if selection takes place in a sludge-based medium (not supplemented with the donor strain's special nutrient), the sludge-derived bacteria will grow preferentially, favoring selection of the modified reporter-expressing sludge bacteria. An example of a selecting step is provided below in the Examples section, but it is understood that other known selection conditions (e.g., antibiotic resistance) can be used or routinely modified for use in selecting the present signal-expressing sludge bacterium over the unmated signal expressing donor cells.

Because of the nature of the sludge mating method, the reporter bacterium can be a modified form of any bacterium contained in the biological sludge. Included among the bacteria known to be present in biological sludges are Zoogloea spp., Pseudomonas spp., Hyphomicrobium spp, Alcaligenes spp., Acinelobacter spp. and Sphaerotilus spp.

See also, *Bergey's Manual of Systematic Bacteriology* (18) and Jenins et al. (19), for fists of such bacteria Other sludge bacteria that have not yet been identified can be subjected to the present mating procedure and can be identified and isolated by the selection step in the method. The key requirement is that the sludge bacteria be able to mate with the donor strain and stably maintain and express the reporter gene construct. The teaching of the mating method and methods of determining that mating of donor and recipient has occurred are provided in the Examples set forth herein. Thus, many reporter bacteria of the invention are routinely developed using the present methods. Indeed, it is not unreasonable to expect to obtain more than one reporter strain from a mating procedure.

The reporter bacterium can express a non-natural reporter protein that produces a visible signal. The visible signal can be light, which can be, for example, in the form of luminescence (i.e., bioluminescence). If the signal is in the form of luminescence, the reporter bacterium can be said to express bioluminescence or to be bioluminescent. The visible signal can also be the result of production of a pigment as a result of expression of nucleic acid encoding the reporter protein. The nucleic acid that encodes the reporter protein can encode more than one protein, the expression of which results in a detectable signal (e.g., bioluminescence). These genes may be simultaneously or sequentially expressed, depending on the promoter which controls their expression within the construct. Thus, the term "reporter protein" can describe one protein that is sufficient to produce the signal, or more than one protein, which when expressed sequentially or simultaneously or with some temporal overlap, produces the signal.

The reporter bacterium of this invention contains a nucleic acid which is a protein-expressing DNA construct. In a specific example of the reporter bacterium of the invention, the nucleic acid that encodes the bioluminescent reporter protein is a lux construct. The lux construct can be the Tn4431 lux transposon, for example, in plasmid pUTK2, downstream of a maintenance promoter. Other possibilities include the lux construct in any known broad host range plasmid (e.g., pRK293) or transposon (Tn5luxAB). Promoterless lux cassettes can be inserted by transposon mutagenesis directly into the recipient chromosome. Recipients expressing high light output could be chosen by visual examination. The identity of the promoter is not generally crucial. In this case, the promoter upstream of the tux genes in Shk 1 is not definitively known, but is believed to be a plasmid maintenance promoter. Additionally, the reporter protein of this invention can be constitutively expressed.

Other reporter proteins will also be effective in the present reporter bacterium. The key is to have a reporter protein that produces a signal that is not normally expressed or is expressed at a different level in biological sludge bacteria. The most commonly used reporter genes are lacZ (B-galactosidase), lux (luciferase) and GFP (green fluorescence protein), which yield a blue pigment product, light emission and green fluorescence, respectively. The lux genes are the reporter genes of choice for many environmental applications, due to rapid response times and ease of conversion of light emission to an electrical signal. GFP and lacZ are more suitable for monitoring of chronic effects iterated over a long period. The reporter protein or complex of choice depends on the particular application. Relevant design considerations include specificity, sensitivity, reliability, response times and cost. Chemical-specific reporter constructs (e.g., nah/lux for naphthalene; tod/lux for toluene), stress detecting reporter constructs (e.g., alg/lux for stress induced exopolysaccharide production) and signal quenching reporter constructs (e.g., lac/lux and kan/lux for general cell damage) are also provided.

There are several desired characteristics of toxicity monitoring reporter bacteria The Shk 1 bioluminescent reporter bacterium has several of these characteristics desirable in a toxicity monitoring system for prescreening of new manufacturing waste chemicals or routine on-line monitoring of influent wastewater and plant effluent. The Shk 1 reporter bacterium has a high growth rate as dispersed cells, which is advantageous for routine preparation of cultures for toxicity determinations. Shk 1 bacteria grow in fill strength synthetic wastewater containing the typical carbon sources being treated at the targeted plant. Methanol, isopropanol and ethylene glycol (used in the Examples provided herein) have been found to be non-inhibitory to wastewater solids, with respirometry-based $EC_{50}$ values ranging from 50 to 200 ml/L (Kilroy and Gray, 1992). Bioluminescence was not affected by settled wastewater solids supemnatant or normal influent wastewater. A decrease in bioluminescence in response to normal concentrations of influent chemicals would suggest that the strain is overly sensitive to potential toxicant effects on wastewater solids quality. In addition, Shk 1 bacteria bioluminescence is unaffected by pH over typical influent pH ranges. A constant bioluminescence response over a wide pH range enables the bioluminescent reporter bacterium to be used at typical wastewater pH. Toxicity monitoring is more difficult using strains with nutritional or environmental requirements inconsistent with the nature of the wastewater being treated.

Thus, the invention flirther provides a method of making a reporter bacterium, comprising contacting a bacteria-containing sample of a biological sludge with a bacterium containing a nucleic acid that encodes a reporter protein that does not naturally occur in a biological sludge bacterium. The nucleic acid can encode a bioluminescent reporter protein, in which case the reporter bacterium is a bioluminescent reporter bacterium. Alternatively, the nucleic acid can encode a non-luminescent signal-producing protein. The reporter bacterium can be selected according to the methods provided herein as well as others. A reporter bacterium, obtained by the above process is provided.

Also provided is a method for making a bioluminescent reporter bacterium, comprising: a) delivering to an isolated biological sludge bacterium, that occurs naturally in a biological sludge, a nucleic acid construct which contains a nucleic acid that encodes a bioluminescent reporter protein that does not occur naturally in the bacterium, under conditions in which the nucleic acid encoding the reporter protein is taken up by the sludge bacterium. This method differs from the sludge mating method in that the particular sludge bacterium to which the reporter protein encoding DNA is delivered according to methods standard in the art for delivering nucleic acid into prokaryotic cells, is first isolated from other sludge components. As described above, any genus/species likely to be present in wastewater sludge could be subjected to this method. Selecting for a reporter bacterium that express bioluminescence can be routinely performed by visual inspection or other method. A bioluminescent reporter bacterium, obtained by the process described above is also provided. Also, as described herein, nucleic acids encoding reporter proteins other than bioluminescent proteins can be used to make the present reporter bacterium.

The delivery step can be carried out by any of the methods known for introducing or inserting nucleic acids into a bacterium. For example, electroporation, transformation and transduction are all routine methods in prokaryotes. Any other routine methods used to deliver DNA to prokaryotes can be tested in the present method. In the reporter bacterium of the invention, the nucleic acid is a protein-expressing DNA construct. The nucleic acid construct can be a plasmid, a tansposon, or a phage which contains a nucleic acid that encodes a reporter protein. For example, a plasmid that contains an origin of replication that supports plasmid replication within the species, or a vector that integrates into the bacterial chromosome and a promoter within the plasmid or chromosomal integration vector operatively linked to the reporter-encoding DNA, are all within the purview of this invention. The requirements for other components of the construct can be routinely determined by reference to molecular methods manuals such as Sambrook et al. (17) or to the literature. The conditions under which the recipient cell takes up the DNA construct can be those described below in Example 1, or others as described in molecular methods manuals such as Sambrook et al. (17). The reporter protein can be as described above.

In the reporter bacterium of the invention, the reporter protein can be constitutively expressed. This would be the case with quench-specific reporter bacteria like the Shk 1 reporter bacterium, but other reporter bacteria can be made to function as probes to detect particular toxicants or other sludge components. Different types of genetic constructs have been used in reporter bacteria, depending on the application. Of particular relevance to the problem of toxic shock are chemical-specific, stress-specific and quench-specific reporter bacteria. Chemical-specific reporter bacteria are designed to detect a specific chemical or group of chemicals. They can also be used to determine if conditions are favorable for biodegradation of the target chemical, as the genetic control elements are based on microbial degradative pathways. Examples of this type of probe include nah/lux for naphthalene and tod-lux for toluene. Stress-specific reporter bacteria are used to determine if microorganisms are experiencing environmental conditions sufficiently adverse to activate damage control or defensive responses. An example of a stress probe is alg-lux, which would be expressed when exopolysaccharides, produced in response to high ethanol concentrations, high salnity or nitrogen limitation, cause gene expression via promoter induction. The lux genes are placed downstream from the promoter.

Quench-specific reporter bacteria (cell damage-detecting reporter bacteria) continuously produce a detectable signal. Toxicity is indicated by cellular damage sufficient to impair the general metabolic activities necessary for signal production, resulting in no signal detection or a reduced amount of signal detection relative to the amount of signal detection in non-toxic conditions. The bioluminescent reporter bacterium Shk 1 is an example of a quench-specific reporter bacterium.

A method of detecting the presence of toxicity in a wastewater treatment influent stream is also provided. This method comprises: a) contacting the influent with a reporter bacterium that expresses a reporter protein; b) detecting the expression of the reporter protein by the reporter bacterium; and c) correlating a reduction in the expression of the reporter protein with the presence of toxicity. In one embodiment of the present invention, the expression of the reporter protein by the reporter bacterium can be by detecting and measuring the light output from a bioluminescent reporter protein, such as luciferase. In a more specific embodiment, the present method for detecting a toxic condition of a wastewater fluid in a biological wastewater treatment facility having an influent stream of wastewater fluid, involves: a) diverting a stream of fluid from the influent stream to a contact chamber, b) adding the bioluminescent reporter bacterium of the present invention to the contact chamber containing the fluid from step (a); and c) detecting light output from the contact chamber, a reduction in light output indicating a toxic condition.

For example, light emission from reporter bacteria employing light emitting reporter proteins is transmitted through optical fibers to light multiplying devices and sensors. The degree of signal amplification required depends to some extent on both the reporter bacteria design and the strength of the environmental stimulus. Reporter responses can be compiled and stored using computer data acquisition software. Process control responses (e.g., diverting or reducing the flow of a toxic wastewater influent in a wastewater treatment system) can be automatically or manually activated based on set point alarms. Levels of light emission, which trigger process control responses can be calibrated empirically with influent characteristics expected to cause toxic shock.

The present invention also contemplates the use of a bioluminescent reporter bacterium of this invention in a method for detecting a toxic condition of a wastewater fluid in a biological wastewater treatment facility having an influent stream of wastewater fluid, comprising: diverting a stream of fluid from the influent stream to a contact chamber, adding the reporter bacterium of this invention to the contact chamber containing the diverted fluid from the influent stream; and detecting light output from the contact chamber using a device for detecting light output, such as, for example, a liquid light pipe or a fiber optic cable for transmitting light, coupled to a device for measuring the transmitted light, such as a photomultiplier or photodiode; whereby a reduction in light output indicates a toxic condition.

A liquid light guide and a fiber optic tube or cable are devices which provide a means of transmitting light from the sampling location to the location of conversion of light to an electric signal. Light is transmitted through the fibers in the fiber optic tube or through the liquid light guide (a tube filled with clear liquid) by internal reflection. The light is converted to a measurable electrical signal (current) at the detector (photomultiplier or photodiode). Changes in the electrical signal reflect changes in the quantity of light. A photomultiplier consists of a photoemissive detector that frees an electron when bombarded with a photon of light. An amplified electrical current is then produced. A photodiode is a light sensitive semiconductor component that produces an electrical signal in response to light.

The method of the present invention for detecting a toxic condition of a wastewater fluid in a biological wastewater treatment facility having an influent stream can further comprise: adding a bioluminescent reporter bacterium of the present invention to a chamber that does not contain a wastewater fluid diverted from the influent wastewater stream; detecting light output from the chamber by a device for detecting light output, such as, for example, a liquid light pipe or a fiber optic line for transmitting light, coupled to a device for measuring light, such as a photomultiplier or photodiode; and comparing the light output detected in the contact chamber containing the diverted fluid from the influent stream with the light output detected in the chamber that does not contain a wastewater fluid diverted from the influent wastewater stream. A relative reduction in light output in the contact chamber containing the diverted fluid from the influent wastewater stream as compared to the chamber that does not contain a wastewater fluid diverted from the influent wastewater stream indicates a toxic condition in the wastewater fluid. The chamber that does not contain a wastewater fluid diverted from the facility can contain synthetic wastewater. It is reasonable to expect that the light output from the reporter bacterium can be standardized in a way that permits the detection of toxic influent without requiring comparison to a control.

In another embodiment, the present invention provides a method for determining the effect of a known dose of an oxidative phosphorylation decoupling agent on biological wastewater sludge, comprising: contacting a sample of the sludge, containing a known dose of the decoupling agent, with a bioluminescent reporter bacterium of the present invention; contacting a sample of the sludge, not containing the decoupling agent, with a bioluminescent reporter bacterium of the present invention; detecting light output by the reporter bacterium in the sludge sample containing the decoupling agent; detecting light output by the reporter bacterium in the sludge sample not containing the decoupling agent; and comparing the light output by the reporter bacterium in the sludge sample containing the decoupling agent with the light output by the reporter bacterium in the sludge sample not containing the decoupling agent. A decrease in light output by the reporter bacterium in the sludge sample containing the decoupling agent, as compared with the light output by the reporter bacterium in the sludge sample not containing the decoupling agent, can be correlated with an action of the decoupling agent, whereby the effect of the known dose of the decoupling agent is determined. It is reasonable to expect that the light output from the reporter bacterium can be standardized in a way that permits the measuring of a decoupling agent's effect without requiring comparison to a control. It is also contemplated that a reporter bacterium of the present invention that utilizes a signal other than a bioluminescent signal can be used in any of the above detection methods, and the signal detected using means described in the art for detecting the chosen signal.

Uncouplers and inhibitors of electron-transport phosphorylation are known in the art. A variety of chemical agents, called uncozplers, inhibit the synthesis of ATP during electron transport without inhibiting the electron-transport process itself Examples of such uncoupling agents are dinitrophenol, dicumarol, carbonylcyanide-m-chlorophenylhydrazone, and salicylanllide. All of these agents are lipid-soluble substances that are acidic and can pass through the lipid matrix of the membrane when combined with Hydrogen atoms. These substances promote the passage of $H^+$ ions across the membrane, causing dissipation of the proton-motive force. Characteristically, uncouplers actually stimulate respiration, while completely inhibiting ATP synthesis, thus resulting in wasted energy.

Various chemicals inhibit electron transport by interfering with the action of electron carriers. Carbon monoxide combines directly with the terminal cytochrome, cytochrome oxidase, and prevents the attachment of oxygen. Cyanide (CN—) and azide ($N_3$—) bind tightly to the iron of the porphyrin ring of the cytochromes and prevent its oxidation and reduction. The antibiotic antimycin A inhibits electron transport between cytochrome b and c. All of these inhibitors and uncouplers are powerfuil poisons for cells, inhibiting growth and other functions (16).

Bacteria in the wastewater treatment facility convert the waste chemicals in the influent into $CO_2$ and new cell mass, thereby resulting in an effluent free of potential environmental contaminants. The cell mass settles in the clarifier, from which a portion is recycled to the head of the plant and a portion is disposed of via incineration or some other means. Since sludge (waste cells) disposal is expensive, it is desirable to reduce the cell yield to only that needed for maintaining the necessary populations for chemical degradation in the plant. The addition of decoupling agents results in a greater portion of the waste being transformed to $CO_2$ than cells. However, controlling the dose of decoupling agents, which are toxicants, is necessary. Too high a dose will kill the cells and destroy the function of the plant and too low a dose will result in excess cell yield.

The present reporter bacteria can be used for monitoring both the influent wastewater (potential source of unknown or unplanned toxicant addition) and the chamber (e.g., aeration basin) to which decoupling agents are being added. If a toxic event is indicated in the influent, it would be desirable to stop adding the decoupling agent to allow the microorganisms all possible energy production for repair of toxdcant damage and replenishment of killed cells by new cell growth. Addition of the decoupling agent can be resumed once the system has recovered from the unplanned toxicant addition. It is also reasonable to use the present methods and reporter organisms to monitor sludge energetics at one point in the system and the presence of potential toxicants at another point.

The light output of the bioluminescent reporter bacterium with or without contact with the decoupling agent can be determined according to the methods described herein for measuring light output of bioluminescent microorganisms. The reporter bacteria can be any of the reporter bacteria of this invention. The decoupling agent can be, but is not limited to those listed above, as well as any other decoupling agents now known or identified in the fuiture. One or more decoupling agents can be used sequentially or in combination in the present invention.

The effect of the decoupling agent can be either an increase or a decrease in signal (e.g., light/bioluminescence) output by the reporter bacterium. An increase in signal output by the reporter bacterium which has been contacted with the decoupling agent as compared to the signal output of the reporter bacterium that has not been contacted with the decoupling agent indicates increased energy production by the reporter bacterium contacted with the decoupling agent. A decrease in signal output by the reporter bacterium which has been contacted with the decoupling agent as compared to the signal output by the reporter bacterium that has not been contacted with the decoupling agent indicates decreased energy production by the reporter bacterium contacted with the decoupling agent.

A determination of the amount of energy production by the reporter bacterium as a result of contact with a decoupling agent is desirable in order to monitor the effects of the decoupling agent on sludge energetics. For example, it is desirable to control sludge energetics by adding decoupling agents which have the effect of reducing energy yield by the sludge microorganisms, thereby reducing sludge yield. This reduction in sludge yield is helpful in minhnling sludge disposal problems at wastewater treatment plants. Due to variations in wastewater influent composition, variability in activated sludge microbial activity and declining effectiveness due to degradation of the decoupling agents by adapted microorganisms, it is not practical to use standard doses of decoupling agents. Insufficient doses will not result in adequate decoupling of oxidative phosphorylation, whereas excessive doses will kill the activated sludge microorganisms, resulting in problems with sludge quality, inactivation of wastewater treatment effectiveness or wash-out of the plant. Therefore, it is most desirable for efficient operation of the wastewater treatment plant to maintain an amount of a decoupling agent in the sludge which provides a consistent level of energy yield by the sludge microorganisms which does not rise above nor fall below threshold values.

Thus, the present invention also contemplates a method for continuously regulating the energetics in biological wastewater sludge, comprising: continuously monitoring the effect of a known dose of a decoupling agent in a wastewater sludge sample according to the method described above for determining the effect of a known dose of a decoupling agent on sludge energetics; and continuously increasing or reducing the dose of decoupling agent to maintain a selected output of light by the reporter bacterium. In the case of a bioluminescent reporter bacterium, the selected output of light by the reporter bacterium is that output of light achieved when the activated sludge bacteria are producing a level of energy which has been determined to be ideal for producing a desired yield of sludge mass. The desired energy level/light output can be routinely determined empirically as the level of light seen at a dose which does not result in an increase or a decrease in the sludge mass in the plant. It is also contemplated that a reporter bacterium of the present invention that utilizes a signal other than a bioluminescent signal can be used in any of the above detection methods, and the signal detected using means described in the art for detecting the chosen signal.

To carry out the above-described method, an apparatus for detecting a toxic condition in a wastewater influent at a biological wastewater treatment facility is provided. The apparatus can comprise: a) a first chamber, containing a bioluminescent reporter bacterium of the present invention; b) means in fluid communication with the first chamber for diverting a portion of the wastewater influent into the first chamber, and c) means in photometric proximity to the first chamber for detecting light output from the bioluminescent reporter bacterium, whereby a reduction in light output detects a toxic condition. The apparatus can further comprise a second chamber containing a control medium and the biolumiescent reporter probe. The control medium can be a stream of synthetic wastewater, to which the biolumiescent reporter bacterium of this invention can be mixed. The present apparatus can be routinely adapted for use with reporter bacterium that produces a detectable signal other than light, for example by substituting calorimetric equipment for the light detecting equipment when the signal is a color change.

The wastewater fluid can be delivered to the first chamber as a single, main stream or as split stream which has been diverted from the main stream of wastewater fluid. The first chamber of the apparatus of the present invention can be in fluid communication with an aeration basin or an equalization basin. A diversion basin can be present in the treatment system in anticipation of the need to divert an influent strain that is found to contain a toxic substance. For example, in a wastewater treatment system which contains an equalization basin, a toxic response can be detected in sludge delivered to the detection chamber from the equalization basin. In a system which lacks an equalization basin and comprises an aeration basin, a toxic response can be detected either in sludge diverted from the aeration basin, or in sludge diverted from the influent stream.

As used herein, a means to receive, deliver or divert fluid is a means by which the receipt or delivery of the fluid can be controlled by means of a valve or other device which allows delivery or receipt to be stopped or started as desired.

For example, under normal wastewater treatment operations, receipt of the wastewater into the aeration basin or equalization basin is allowed because the valve(s) or other flow regulating device(s) are opened. Receipt of the wastewater into the diversion chamber and delivery of wastewater from the diversion chamber back into the normal processing chambers is controlled by valve(s) or other regulatory device (s). If a toxic response is detected in the wastewater influent stream, the toxic influent stream from the treatment facility can be diverted directly to the diversion chamber by closing the valve(s) or other regulatory device(s) that allow entry of fluid into the aeration basin or equalization basin and by opening the valve(s) or other regulatory device(s) that allow entry of fluid into the diversion chamber. The flow of the toxic influent stream from the diversion chamber into the aeration basin or equalization basin can then be regulated in order to minimize the effect of the toxic influent on the activated sludge in the wastewater treatment system by controlling the flow rate or the number of valves or regulatory devices opened between the diversion chamber and the aeration basin or equalization basin.

The reporter bacterium used in the apparatus can be the reporter bacterium of the present invention. The reporter bacterium can be produced or maintained in a chemostat or turbidostat (either manual or automatic) in which bacteria are continuously produced and from which they are fed into the first chamber of the detection apparatus where they are mixed with the wastewater influent. In the case of a bioluminescent reporter bacterium, the amount of light produced by the biolurniescent reporter bacterium when in contact with the wastewater influent in the first chamber can be continuously measured by a light detection device, such as, for example, a liquid light pipe or a fiber optic cable. The means to detect light, i.e., the light detection device, is coupled to a means to measure the detected light, which can be, for example, a photomultiplier or a photodiode.

The reporter bacterium can be fed into the second chamber of the detection apparatus where they are mixed with the synthetic wastewater. With the bioluminescent bacterium, the production of light by the biolumiescent reporter bacterium in the synthetic wastewater can be continuously measured with the light detecting devices described above for light output comparison with the biolumiescent reporter bacterium in contact with the influent wastewater being tested for toxicity. The amount of light detected in the second chamber, or control chamber, can be used to correct for any variation in the metabolic condition of the bioluminescent reporter bacterium. These light output data can be applied, via appropriate algorithms, to monitor the effect of diverting or controlling addition of a toxic influent to activated sludge in a wastewater treatment system and thereby minimize harmfutl effects of the toxic waste.

An example of an appropriate algorithm could include the following: 1) If a decrease in light from the sample chamber as compared to the control chamber is detected, the incoming waste stream is diverted to a temporary holding basin— to be returned to the treatment aeration basin at a rate which does not damage sludge quality, and 2) When the light from the sample chamber returns to the same level of light as in the control chamber, the incoming waste stream can be returned to the regular flow path (e.g., to the aeration basin).

The continuous monitoring of light output of the biolumiescent reporter bacterium as well as the maintenance of a consistent output of light by the reporter bacterium can be achieved by the use of an apparatus for monitoring the effect of a decoupling agent on sludge energetics in a biological wastewater treatment facility. The apparatus can comprise a) a first chamber, containing a reporter bacterium of claim 1–15 for receiving a portion of a biological sludge; b) means in fluid communication with the first chamber for diverting a portion of the biological sludge to which a decoupling agent has been added, into the first chamber, and c) means in photometric proximity to the first chamber for detecting light output from the reporter bacterium, whereby a reduction in light output correlates with the effect of a decoupling agent on sludge energetics. Similarly, the continuous monitoring of non-light signal output of the reporter bacterium as well as the maintenance of a consistent non-light signal output by the reporter bacterium can be achieved by the use of the above-described apparatus, modified to include means for monitoring the effect of a decoupling agent on the non-light signal output.

The configuration of the wastewater treatment system and the use of the decoupling action detecting apparatus are essentially as described above for use of the toxicity monitoring apparatus. The exact configuration of the wastewater treatment facility is not crucial to the use of the present apparatus or reporter bacterium and methods. Thus, the present invention can be applied in virtually any wastewater treatment plant.

When a bioluminescent reporter bacterium is used, the amount of light produced by the bioluminescent reporter bacterium when in contact with the activated sludge and decoupling agent in the first chamber can be continuously measured by a light detection device, such as, for example, a liquid light pipe or a fiber optic line. The means to detect light, i.e., the light detection device, is coupled to a means to measure the detected light, which can be, for example, a photomultiplier or a photodiode. The control chamber can receive a stream of activated sludge (in the absence of decoupling agent), to which the bioluminescent reporter bacterium of this invention can be mixed. The production of fight by the bioluminescent reporter bacterium in the activated sludge can be continuously measured with the light detecting devices described above for light output comparison with the bioluminescent reporter bacterium in contact with the activated sludge and decoupling agent.

With the use of this apparatus, the effect of a particular dose of decoupling agent can be determined and the dose of decoupling agent added to the wastewater treatment system can be adjusted accordingly to maintain the sludge microorganisms in a condition of optimum metabolic activity with a minimum cell yield. The present apparatus can be routinely adapted for use with reporter bacterium that produces a detectable signal other than light, for example by substituting calorimetric equipment for the light detecting equipment when the signal is a color change.

The following examples are intended to illustrate, but not limit, the invention, since numerous modifications and variations therein will be apparent to those skilled in the art. While the protocols described are typical of those that might be used, other procedures known to those skilled in the art may be alternatively employed.

EXAMPLE 1

Bioluminescent Reporter Construction

*Escherichia coli* containing plasmid pUTK2 (Burlage et al., 1990), with the Tn4431 lux transposon downstream of a putative plasmid maintenance promoter, was mated with bacteria in wastewater solids obtained from a wastewater treatment plant. Matings were performed by spreading wastewater solids and *E. coil* cultures containing the bioluminescent plasmid on R2A medium and incubating at 32° C. for 48 hr. A control mating contained only *E. coil* or wastewater solids. Selection for trazsormants was performed on a minimal salts medium, with a chemical composition similar to the influent wastewater, containing 20 ml/L tetracycline and 2,000 ml/L ethylene glycol. One isolate emitting visible light (Shk 1) was chosen for further study.

Small subunit (16S) ribosomal DNA sequencing was used to taxonomically characterize the wastewater solids isolate. The 16S rDNA between base pairs 1114 and 1492 was amplified by PCR using primers 1114f and 1492 (Lane, 1991). The amplified DNA was cloned into the TA cloning vector (pCRII) using the manufacturer's protocol (In Vitrogen, San Diego, Calif.). The DNA sequence was determined by single primer extension with 1492r primer (Retrogen, Inc., San Diego, Calif.). The resulting 16S rDNA sequence was screened against the Illinois Ribosomal Data Base using the program Similarity Rank (Maidak et al., 1994).

Screening of the 16S rDNA sequence of the Shk 1 bioreporter against the Illinois Ribosomal Data Base indicated that it belongs to the genus Pseudomonas with a similarity of 0.817 to Pseudomonas flavescens strain B62 (Hildebrand et al., 1994). The Shk 1 bacteria grew in the synthetic wastewater as dispersed cells with a doubling time of approximately 2.2 hr.

Bioluminescent Response to Toxicants in Batch Tests

The initial bioluminescent response of Shk 1 bacteria to a range of pH conditions, cadmium, ethanol, hydroquinone and 2,4-dinitrophenol concentrations was measured using a MICROBETA Liquid Scintillation Counter (Wallace, Inc., Gaithersburg, Md.). A time course of the bioluminescent response to hydroquinone concentrations was recorded.

The reporter strain was grown in simulated wastewater medium to a cell density of 0.5 $OD_{600}$. Simulated wastewater medium consisted of salts, metals, phosphorous ($K_2HPO_4$) and nitrogen [$(NH_4)_2SO_4$]. The major carbon sources in the simulated medium were acetate (1,000 ml/L), methanol (108 ml/L), isopropanol (94 ml/L) and ethylene glycol (2,000 ml/L). A concentrated amount of toxicant or pH buffer was added to the MICROBETA scintillation counter plate wells (40 $\mu$l) and then reporter cells were added (160 $\mu$l). Immediately after the addition of cells, bioluminescence was measured from the wells with the scintillation counter.

The range of pH examined was 5.5–7.9, while concentrations of ethanol, cadmium, hydroquinone and 2,4-dinitrophenol ranged from 0 to 10,000 ml/L. All samples were prepared in triplicate. Hydroquinone toxicity was assessed in distilled water, simulated wastewater and in wastewater solids from bench scale reactors.

Figure 2:
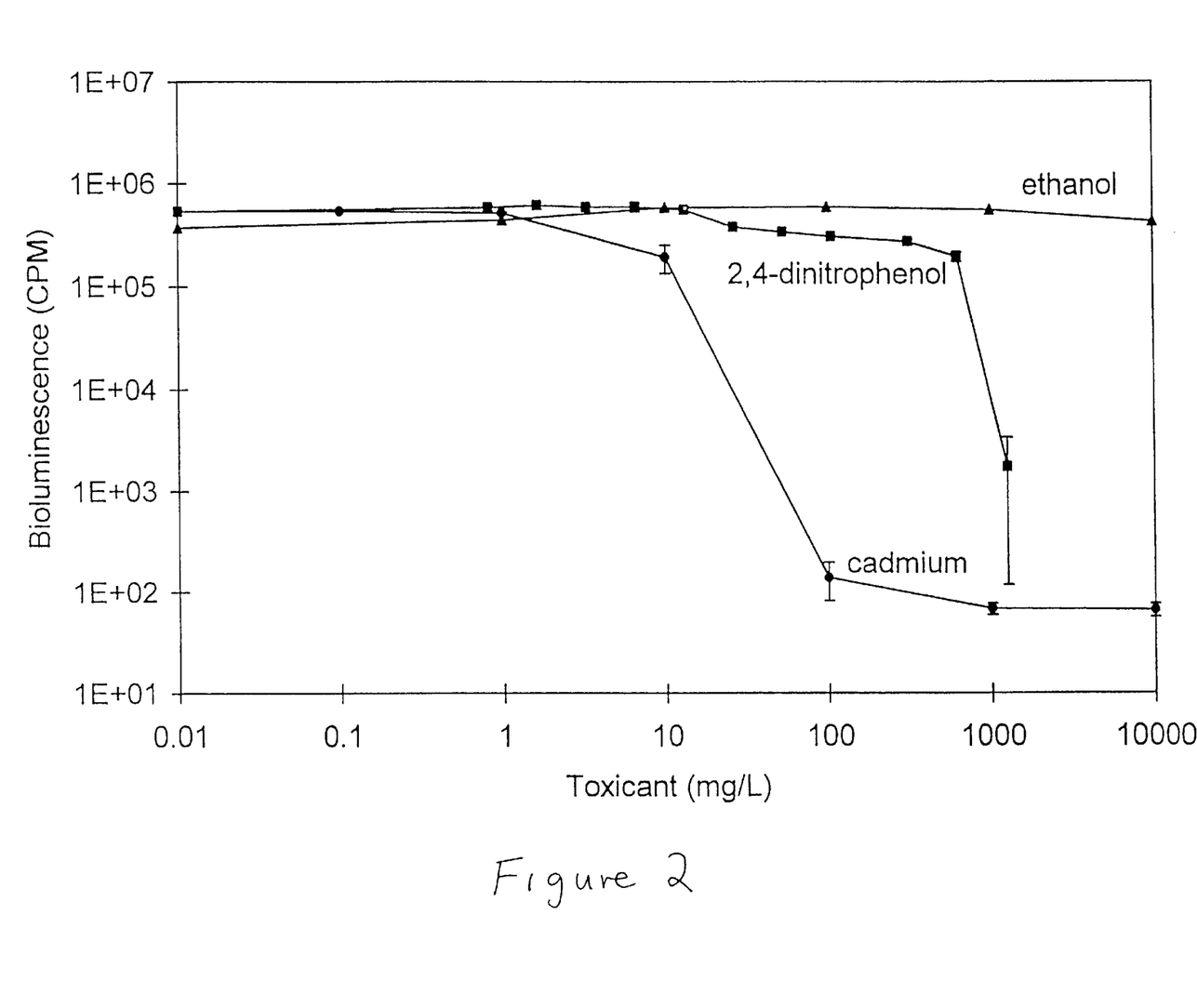
FIG. 2 shows the bioluminescent response of the Shk 1 reporter bacterium to toxicants ethanol (Δ), 2,4-dinitrophenol (■) and cadmium (●).

The bioluminescence of the Shk 1 reporter strain decreased in response to the toxicants cadmium, 2,4-dinitrophenol and hydroquinone. In contrast, concentrations of ethanol up to 10,000 ml/L had no effect on bioluminescence (FIG. 2). The bioluminescent response by the Shk 1 bioreporter was constant between pH 6.1 and pH 7.9. However, at the lowest pH tested (pH 5.5), bioluminescence was depressed slightly. Bioluminescence decreased with increasing cadmium concentration greater than 1.0 ml/L (FIG. 2). There was a significant drop in bioluminescence between 1.0 and 10 ml/L and at cadmium concentrations of 100, 1,000 and 10,000 ml/L, bioluminescence was completely inhibited. The bioluminescent response to 2,4-dinitrophenol remained constant with increasing concentration of toxicant until approximately 1,000 ml/L, then decreased sharply (FIG. 2).

Bioluminescence of Shk 1 and Respirometiy of Wastewater Solids in Response to Hydroquinone.

Oxygen consumption rates by industrial wastewater solids upon exposure to hydroquinone were measured. Wastewater solids were obtained from an industrial wastewater treatment plant and placed in 500 ml flasks. The flasks were incubated overnight with 50 ml of simulated wastewater medium. Three ml of the wastewater solids solution, 1 ml of an appropriate hydroquinone solution, and 1 ml of simulated wastewater medium were added to the respirometer well. The oxygen probe (Yellow Springs Instrument, Co., Yellow Springs, Ohio.) was immediately placed over the sample, allowing no head-space in the well, and oxygen concentration was measured over time.

Figure 3:
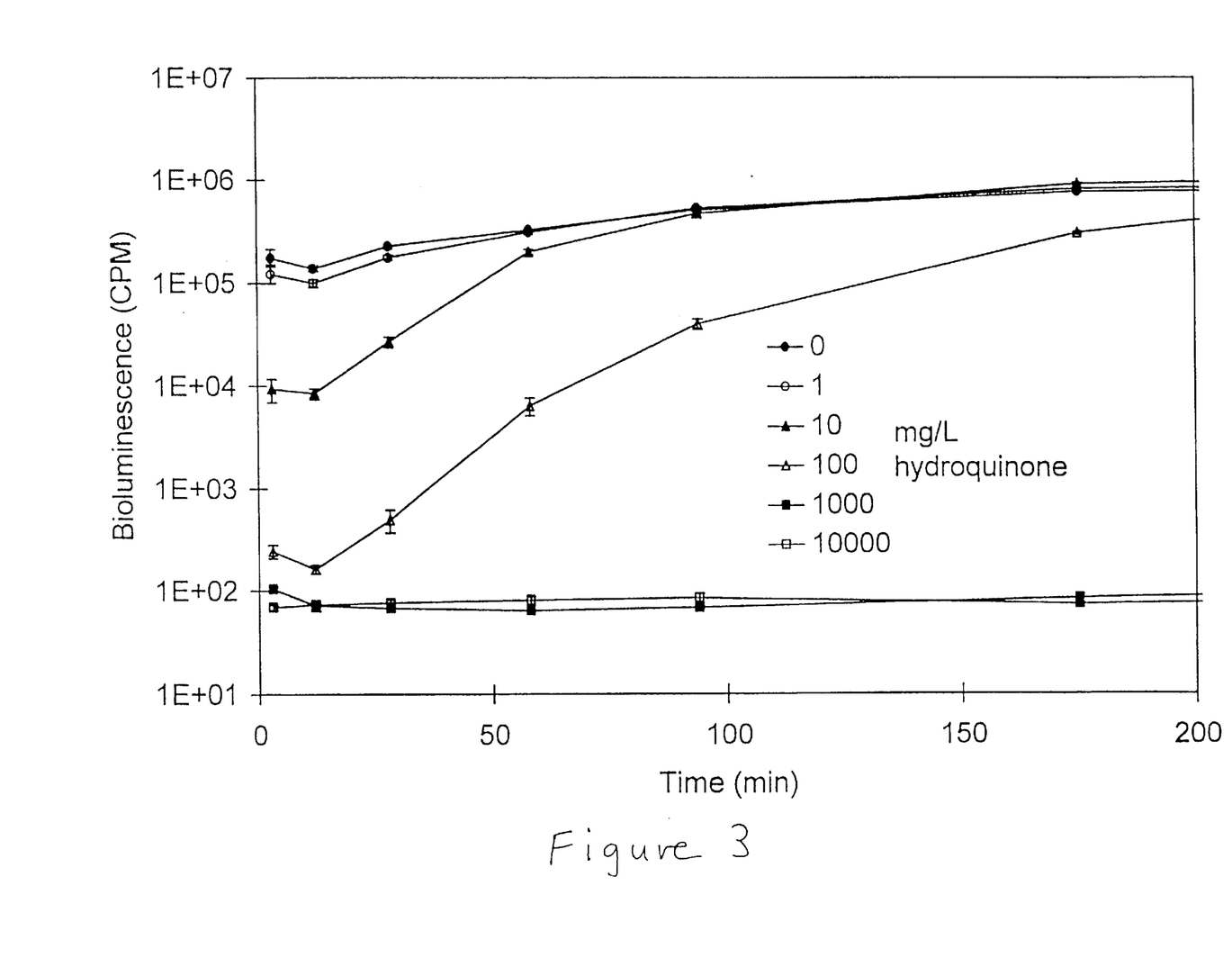
FIG. 3 is a time course of the bioluminescent response by the Shk 1 reporter bacterium to a range of hydroquinone concentrations.

The initial level of bioluminescence of Shk 1 decreased with increasing hydroquinone concentration in each of the matrices examined: Shk 1 with distilled water, simulated wastewater and simulated wastewater with wastewater solids from bench scale wastewater solids reactors. Data from Shk 1 bacteria with simulated wastewater with wastewater solids is presented (FIG. 3). A toxic response was evident at hydroquinone concentrations above 1.0 ml/L. However, the 1.0, 10, and 100 ml/L samples recovered to the 0 ml/L hydroquinone concentration bioluminescence levels in four hours (FIG. 3). Bioluminescence from the 1,000 and 10,000 ml/L samples did not increase by four hours. In previous studies, toxicity to phenol was shown to decrease with increasing incubation time, indicating recovery of bioluminescence (Dutka et al., 1983).

Figure 4:
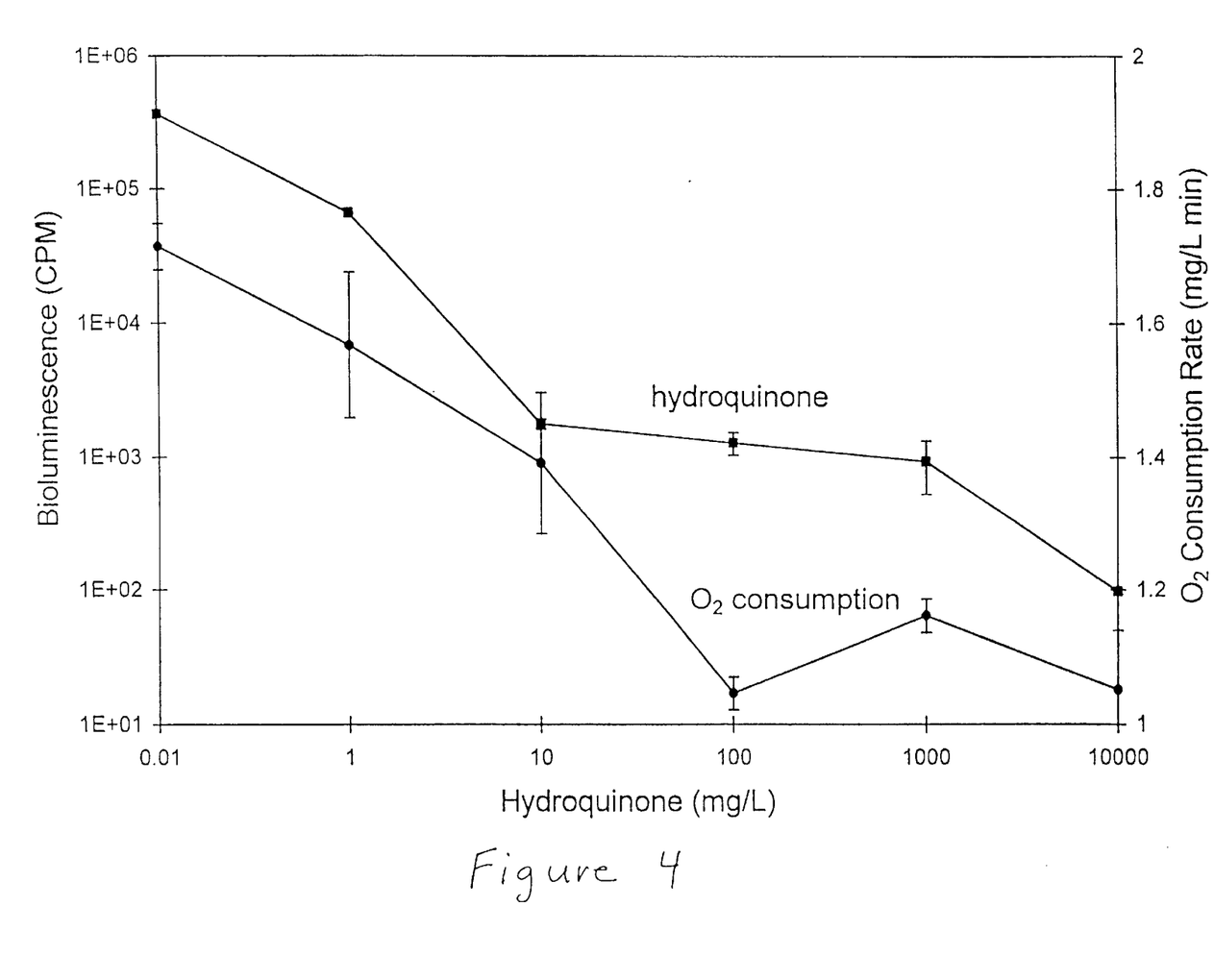
FIG. 4 shows the bioluminescent response by the Shk 1 reporter bacterium and oxygen consumption rate by industrial wastewater solids upon exposure to a range of hydroquinone concentrations. ■ bioluminescence, ● oxygen consumption rate (ml/L min)

Respirometry experiments with industrial wastewater solids resulted in the same general trend in hydroquinone toxicity that was observed with the bioreporter (figure 4). For both bioluminescence and oxygen consumption rate, the decline was dramatic between 0, 1.0 and 10 ml/L hydroquinone, but leveled offbetween 10 and 1,000 ml/L hydroquinone.

Bioluminescent Response to Hydroquinone in a Continuous System

A continuous sampling system was developed to assess the bioluminescent response of the Shk 1 reporter to toxicants (FIG. 1), using hydroquinone as the test toxicant. The sampling system consisted of two light tight sampling vessels with 5 ml of liquid volume and 20 ml of air head-space. A liquid light guide was connected to the top of each vessel that transferred the light to a photomultiplier (Oriel Corp., Stratford, Conn.), where the light signal was converted to an electrical current.

Figure 1:
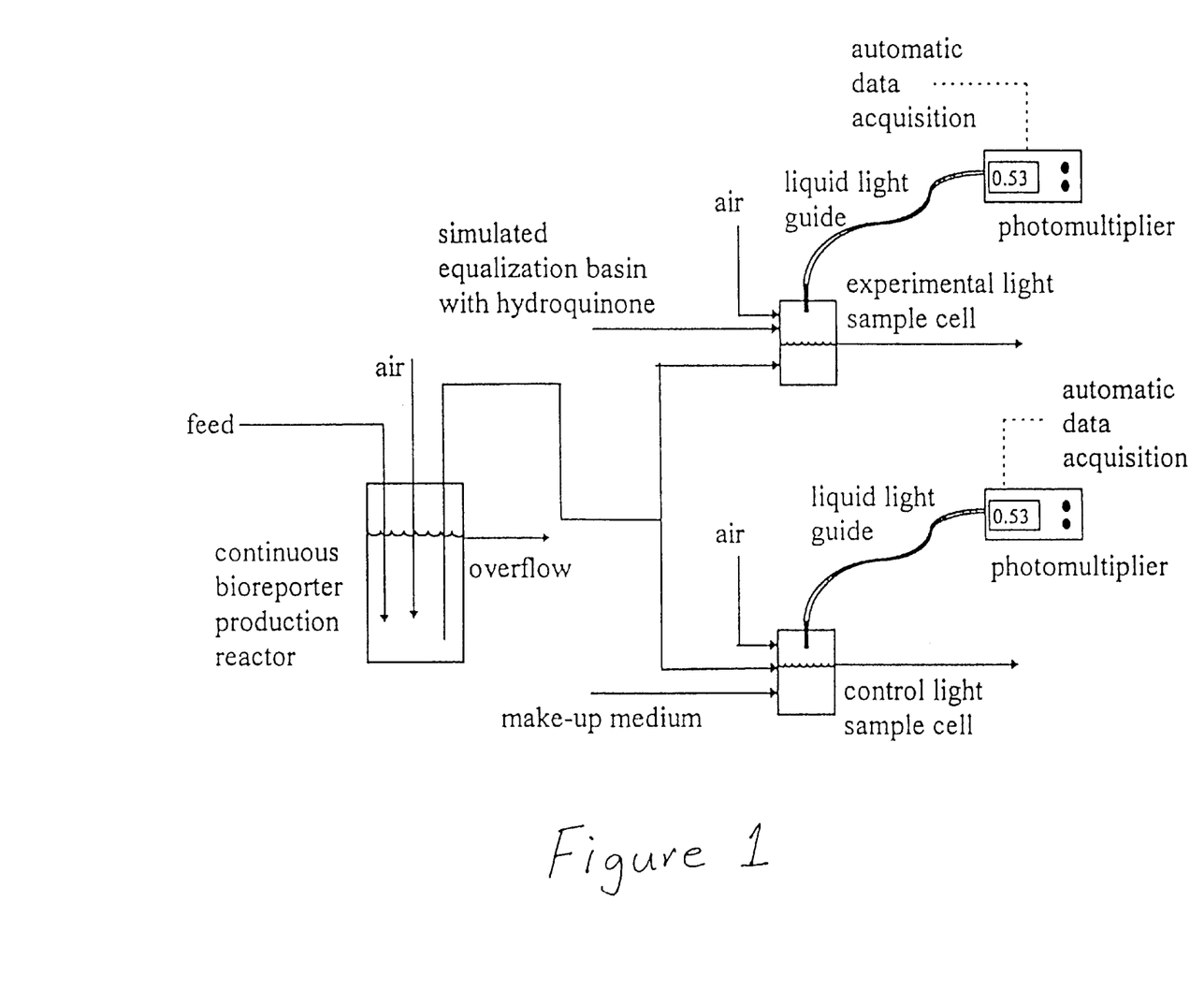
FIG. 1 is a schematic of a continuous sampling system to measure the bioluminescent response by the present Shk 1 reporter bacterium to toxicants. The system includes control and experimental sampling cells.

A batch (25 ml) of reporter Shk 1 cells was added to a 50 ml vessel. Medium was added at a rate sufficient to maintain a constant cell density and these reporter cells were fed to the sample vessels via a peristaltic pump. Air was also provided to each sampling vessel. The control vessel received simulated wastewater, while the experimental vessel received simulated wastewater with sequential intermittent hydroquinone additions at concentrations of 10, 100, 1,000 and 10,000 ml/L.

Figure 5:
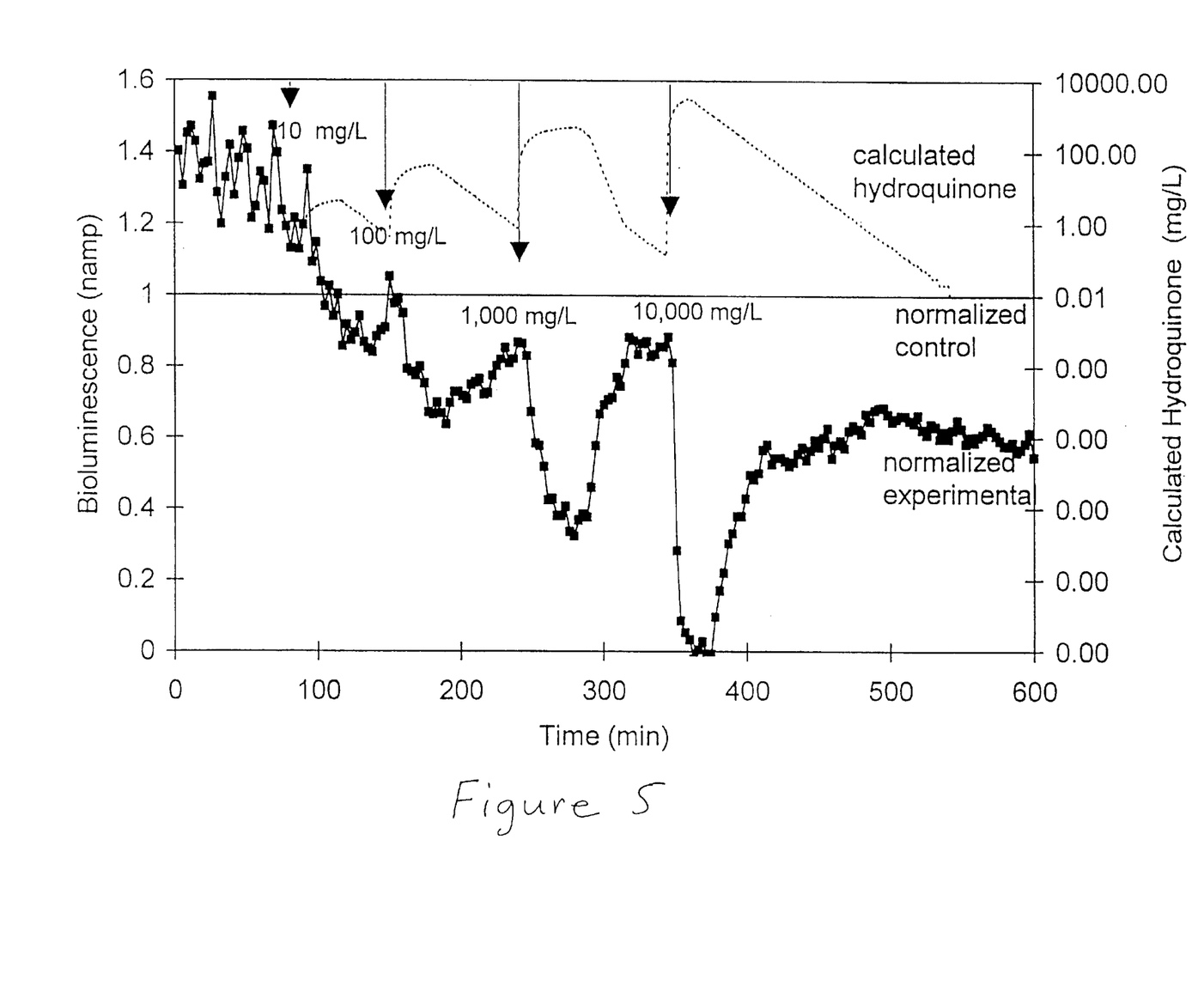
FIG. 5 shows the bioluminescent response of the Shk 1 reporter bacterium to a range of hydroquinone concentrations in the continuous sampling system. The calculated hydroquinone concentration in the experimental sampling cell is indicated. ■ normalized experimental bioluminescence, —normalized control bioluminescence, —calculated hydroquinone concentration (ml/L) in the experimental sampling cell.
Figure 6:
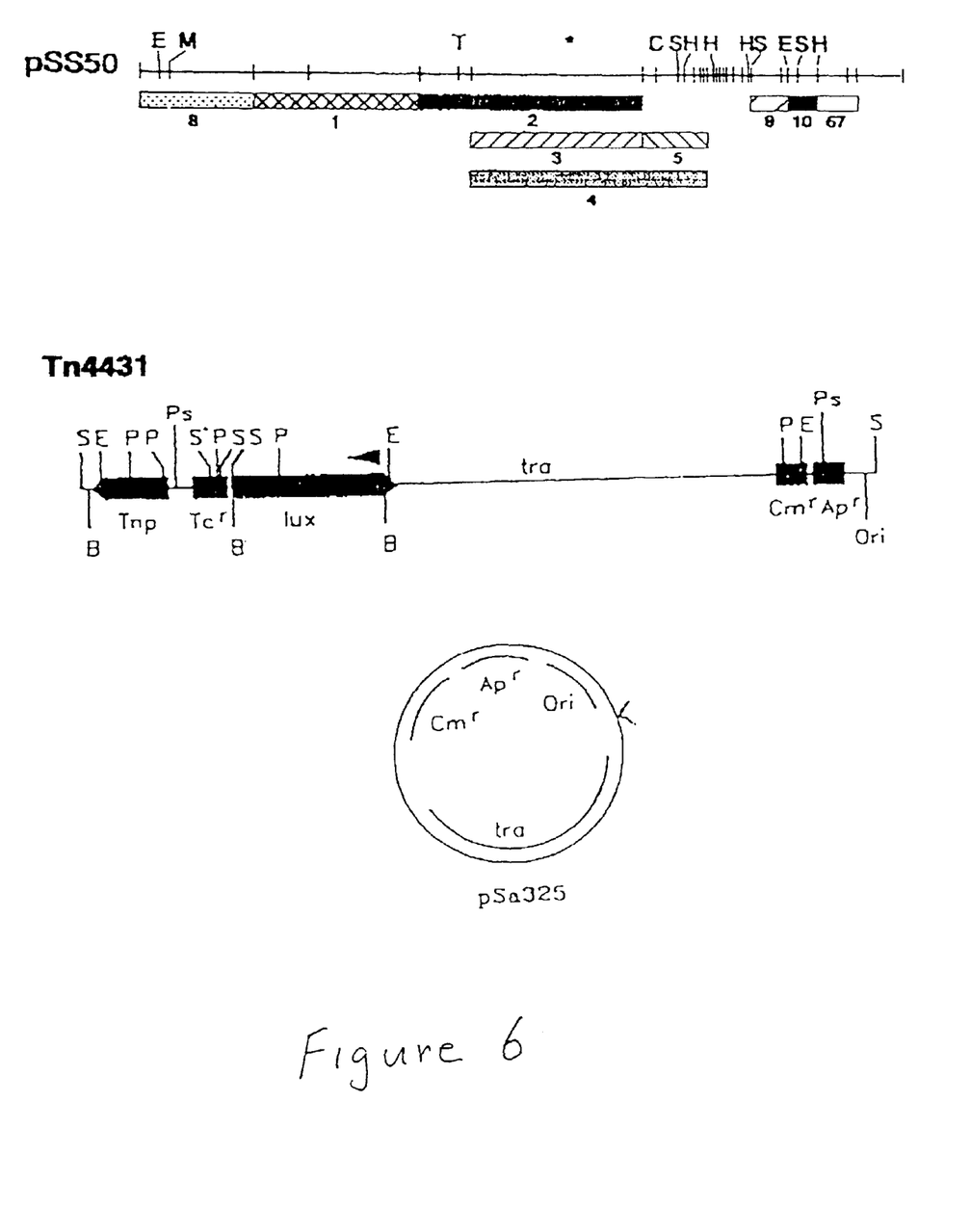
FIG. 6 depicts the genetic constructs pSS50 and Tn4431 and plasmid pSa325 used in an embodiment of the present invention.
Figure 7:
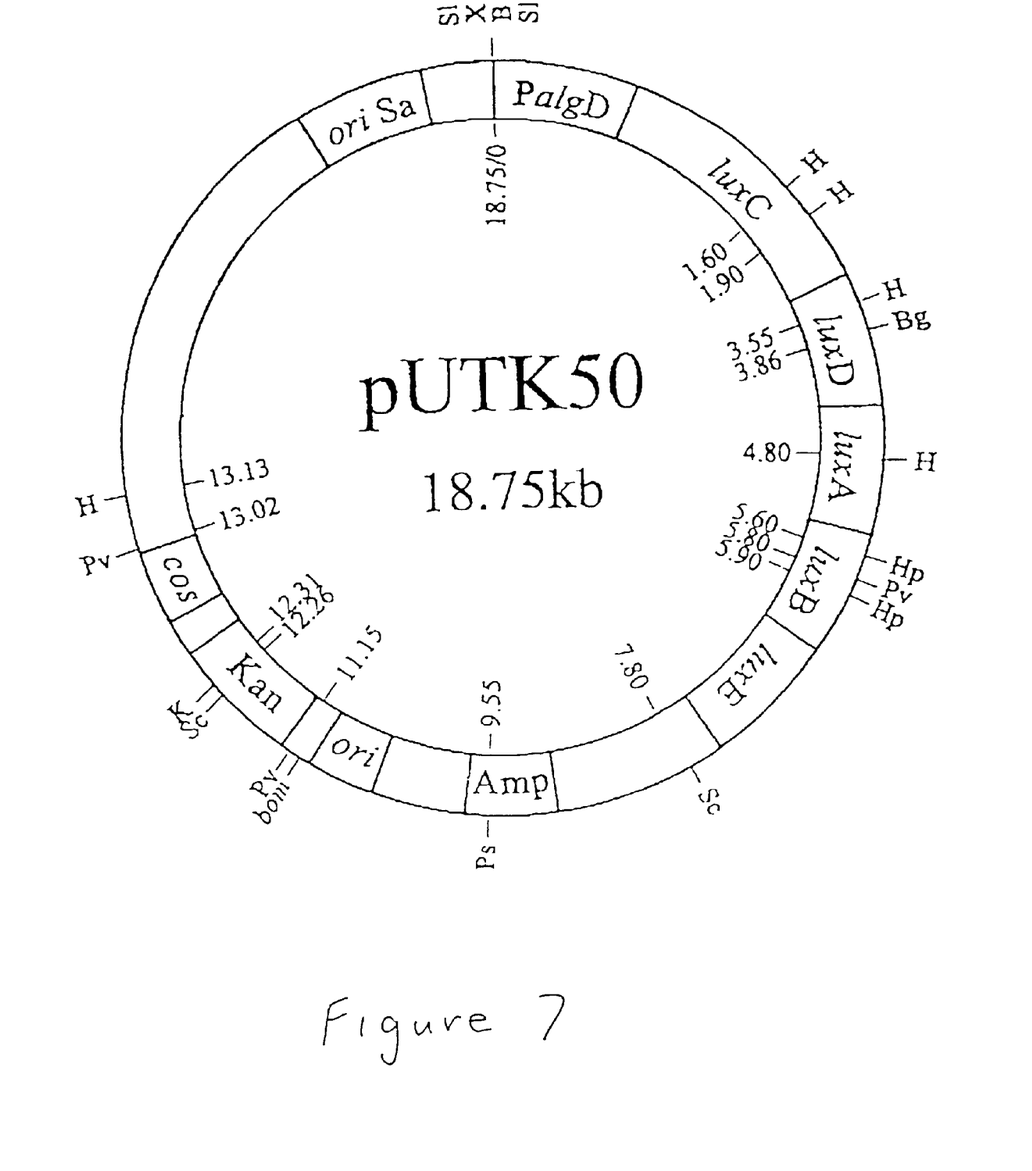
FIG. 7 depicts the plasmid pUTK50 used in an embodiment of the present invention.

Although Shk 1 cells were produced continuously, starting with a batch culture, the control light signal continued to increase throughout the continuous sampling experiment. To account for this, the control and the experimental signal were normalized by the control signal. The normalized light response by the Shk 1 reporter declined during each exposure period to hydroquinone. The declines in bioluminescence corresponded to the calculated hydroquinone concentration in the sample vessel (FIG. 5). The rate of decline in bioluminescence increased with increasing hydroquinone concentration (Table 1), indicating more severe toxic response to a higher concentration of hydroquinone.

Treatment facility-specific bioreporters may be more reflective of potential toxic impact on wastewater solids quality than more generic strains. Light emission from Shk 1 bacteria was sensitive to cadmium, 2,4-dinitrophenol and hydroquinone, which are toxicants known to impact wastewater solids microbial activity (Norberg and Molin, 1983; Battistoni et al., 1993; Volskay and Grady, 1988; Stom et al., 1992). Ethanol, a common component of the influent wastewater, had no impact on light emission in the range tested. In previous studies, the MICROTOX system also demonstrated low ethanol toxicity, with an $EC_{50}$ value for ethanol from 31,000 to 56,706 ml/L (Dutka et al., 1983). However, the $EC_{50}$ value for 2,4-dinitrophenol varied significantly with the type of toxicity assessment. This present study yields an $EC_{50}$ value of 340 ml/L, while Volskay and Grady report an $EC_{50}$ value of 110 ml/L, determined from respirometry (Volskay and Grady, 1988) and Strotmann and Egisaer (1995) reported an $EC_{50}$ value of 29 ml/L, using bioluminescence with *P. phosphoreum* and 70 ml/L via a nitrification inhibition method.

The continuous on-line toxicity monitoring system exhibited rapid and proportional response to increasing hydroquinone concentration. However, normalization of light response using a control chamber was required. Shk 1 culture conditions that yield consistent light output preclude the need for a control chamber. Light monitoring of the Shk 1 culture being supplied to the experimental chamber, rather than the use of a control contact vessel, would further simplify the system.

The ability to insert reporter sequences in a wide array of microorganisms allows for the development of bioreporters tailored for specific applications. In a municipal wastewater treatment plant with tertiary nitrogen removal, nitrifiers may be the most sensitive organisms of concern. In industrial wastewater treatment plants or municipal plants with only secondary treatment, these populations may be of no concern. In these cases, protection of specific degradative organisms for recalcitrant or volatile organics may be of greater importance. In other cases, the only concern may be pin floc resulting from toxicant damage to floc structure. The design of effective bioreporters for toxicity monitoring should include these, as well as other such considerations.

Process Control Responses

The ultimate goal of a toxic shock control strategy is to minimize damage to the wastewater solids communities rather than simply document its occurrence. Process control responses may include diversion of influent wastewater to temporary retention basins followed by gradual addition to the aeration basins at a rate sufficient to avoid toxic concentrations, increase in return wastewater solids to buffer toxic effects and changes in influent flow patterns to minimize localized high toxicant concentrations.

Typical process modifications for countering toxic influent loads include the following: 1) routing of the influent to diversion basins followed by gradual addition to the aeration basin; 2) increasing the return activated sludge flow rate to increase mixed liquor suspended solids (MLSS) in the aeration basin; and 3) changing influent flow distribution to alter the flow regime from plug flow to completely mixed. These are the same responses as would be suitable for transient high loads of non-toxic substrates. Food to mass (F/M) ratios are thereby held constant and toxicity is minimized. These changes in process configuration may be activated using reporter probes.

Due to inherent uncertainties in industrial effluent composition, a "defense in depth" approach is recommended. The amount of time available for assessing the toxicity of the influent wastewater and rerouting to the diversion basins is on the order of seconds to minutes, depending on flow rates and probe location. At this point, quench probes may be most effective due to their rapid response times, the non-specific nature of the response and the potentially high chemical concentrations in the influent. Probes may be located directly in the influent or in a diluted split stream depending on the nature of the influent. Automated in-line TOC (total organic carbon) measurements can also be useful at this point.

Diversion of a potentially toxic influent would allow time to more closely evaluate toxicity, as well as increase MLSS in the aeration basin or alter influent flow distribution. Chemical or stress probes could be used in the diversion basins for further toxicity evaluation. Depending on the retention time available, batch type toxicity testing (MICROTOX) or traditional analytical techniques (TOC, GC) may also be applied. The rate of influent addition from the diversion basins to the aeration basin could be controlled using quench probes or stress probes located in the aeration basin.

The conclusion of the toxic event response could include a return of MLSS to normal levels by decreasing the return activated sludge flow rate, restoration of normal influent flow regimes and monitoring of activated sludge quality by microscopic or molecular analysis to ascertain potential damage.

Initial calibration of reporter probe-generated responses in relation to toxicity levels sufficient to cause toxic shock is desired. This can most effectively be done in batch tests and bench scale activated sludge using influent of known or consistent chemical composition. Further adjustments or modifications may be required at the full scale level.

TABLE 1

Rate of bioluminescence decline upon exposure to hydroquinone in the continuous sampling experiment.

| Hydroquinone concentration (mg/L) | Rate of normalized bioluminescence decline(min-1) |
| --- | --- |
| 10 | 0.011 |
| 100 | 0.013 |
| 1,000 | 0.015 |
| 10,000 | 0.064 |

EXAMPLE 2

Adaptation of Toxicity Monitoring to Individual Wastewater Treatment Plants

Phase I

Reporter constructs according to the invention will be inserted in activated sludge microorganisms from a wastewater treatment plant. These constructs preferably employ light emission as the detectable signal. This will be accomplished by mating donor strains directly with bacteria in mixed liquor from the plant or selected strains isolated from the plant and selection of recipients on a medium derived from the mixed liquor or based on the plant influent. Alternatively, the constructs can be inserted in microorganisms "typical" of activated sludge. This process can be repeated as the content of the influent changes or as the sludge changes over time.

Two of the types of reporter strains that are under consideration are quench probes and stress probes. Quench probes consist of microorganisms which continually emit light. Light emission decreases in response to toxicant damage sufficient to impair the metabolic activities of the cell. This is similar in principle to the MICROTOX assay, but is based on microorganisms relevant to activated sludge at the plant. Previously constructed plasmids of transposon-encoded light emission cassettes can be used to construct these strains.

Stress probes are based directly on the stress responses of microorganisms. Activation of stress responses in the reporter strain is coupled to light emission. Toxicant-induced stress results in an increase in light output. These strains are sensitive indicators of toxic effects as light emission occurs prior to actual cell damage. Currently available cassettes for construction of these strains are based on the algD regulator promoter.

Selected reporter strains constructed in Phase I will be further evaluated in Phase II. The primary criteria for selection are ease of construction, culturability, stability and intensity of light emission.

Phase II

The reporter strains constructed in Phase I will be identified by partial sequencing of the 16S rRNA. Strain identification will be based on comparisons with existing sequences in the Illinois Ribosomal Data Base and GenBank. Oligonucleotide probes based on the 16S rRNA sequence will be synthesized. RNA will be extracted from cells in mixed liquor from the subject plant and probed with an oligonucleotide probe to determine if the reporter strains are representative of the activated sludge microorganisms.

Phase III

Reporter bacteria response to potential toxicants in the subject plant's influent will be determined. Alternatively, influent samples obtained from the plant can be used. Reporter strain responses to different toxicant dosages can be compared with activated sludge activity as determined via respirometry. These experiments can be conducted as single dose batch exposures. Light emission will be quantified using liquid light pipes and photomultipliers. The intensity, speed and duration of light emission in response to toxicant exposure will be determined. Results of these experiments can provide a reasonable basis for determining the potential utility of reporter bacteria strains for monitoring biological activity in activated sludge.

On-line Toxicity Monitoring System.

An on-line system has been developed for monitoring toxicity of wastewater influents to activated sludge and for the controlled addition of potential toxic waste streams. This system uses a split-stream from the activated sludge influent, equalization basin or aeration basin, which is contacted with bioluminescent reporter microorganisms. The microorganisms are continuously produced in a turbidostat and fed into the contact chamber where they mix with the waste stream. A control chamber is used for light output comparison in which the bioluminescent microorganisms are contacted with synthetic wastewater. This corrects for any variation in the metabolic condition of the bioluminescent strains. Light output is continuously monitored via liquid light pipes or fiber optic lines coupled to a photomultiplier, or by photodiodes. Diversion of the influent wastestream, or controlled addition of potential toxicants to minimize adverse effects on sludge quality can be accomplished via suitable control algorithms incorporating light output data.

Bioluminescent reporter sensors can include "typical" sludge microorganisms engineered for bioluminescence according to the protocols provided herein (e.g., Shk 1), or specific microorganisms such as Zoogloea spp., filamentous forms, C1 degraders, etc. Multiple chambers may be used to compare toxicity to different critical populations for the purpose of determining whether toxicants in the influent may select for or against certain microorganism populations.

Activated Sludge Energetics Controller.

Light production by bioluminescent microorganisms is energy dependent Depletion of microbial energy supplies results in declining light output. A control strategy has been designed for monitoring the energy status of activated sludge organisms and adjusting decoupling agent doses accordingly. This is accomplished via monitoring of light output from bioluminescent strains of microorganisms. such as the Shk 1 reporter bacterium of the present invention, using fiber optics and photomultipliers, coupled with a proportional, integral, derivative (PID) controller via suitable control algorithms. In this manner, the sludge microorganisms are maintained in a condition of optimum metabolic activity with a minimum cell yield.

A PID controller is a device which adjusts an output signal (to a speed control of a pump, for example) in response to a change in the measured signal (in this case, the bioreporter light level). A variety of modes can be used that calculate the change in output (P only, PI, or PID). In this case, the controller would adjust the speed of the decoupling agent (for example 2,4-dinitrophenol) addition pump to the activate sludge aeration basin. Further routine experiments with the decoupling agent and the activated sludge system would determine the appropriate light levels and controller mode selection to minimize sludge production.

Throughout this application various publications are referenced within parentheses. Full citations for these publications are as follows. The disclosures of these publications in their entireties are hereby incorporated by reference into this application in order to more fully describe the state of the art to which this invention pertains.

References

1. Battistoni, P., Fava, G., and Ruello, M. L. (1993) Heavy metal shock load in activated sludge uptake and toxic effects. *Water Res.*, 27(5), 821.
2. Burlage, R. S., Bemis, L. A, Layton, A. C., Sayler, G. S., and Larimer, F. (1990) Comparative genetic organization of incompatibility group P degradative plasmids. *J. Bacteriol.*, 172(12), 6818.
3. DuBow, M. S. and Guzzo, A (1992) Luminescent bacterial biosensors to detect toxic agents and elucidate molecular mechanisms of toxicity. Environ Can/et al Proc 15th Int Symp on Wastewater Treatment/4th Workshop on Drinking Water, Montreal,
4. Dutka, B. J., Nyholm, N., and Petersen, J. (1983) Comparison of several microbiological toxicity screening tests. *Water Res.*, 17(10), 1363.
5. Hildebrand, D. C., Palleroni, N. J., Henderson, M., Toth, J. and Johnson, J. L. (1994) *Pseudomonas flavescens* sp. nov, isolated from walnut blight cankers. Int. J. Syst. Bacteriol., 44,410.
6. Jenkins, D., Richard, M. G., and Daigger, G. T. (1993) Manual on the Causes and Control of Activated Sludge Bulking and Foaming. Lewis Publishers, Inc., Chelsea, Mich.
7. Kilroy, A. C. and Gray, N. F. (1992) The toxicity of four organic solvents commonly used in the pharmaceutical industry to activated sludge. *Water Res.*, 26(7), 887.
8. Kong, Z., Vanrolleghem, P., Willems, P. and Verstraete, W. (1996) Simultaneous determination of inhibition kinetics of carbon oxidation and nitrification with a respirometer. *Water Res.*, 30(4), 825.
9. Lane, D. J. (1991) 16S/23S rRNA sequencing. In E. Stackebrandt and M. Goodfellow (eds.), Nucleic Acid Techniques in Bacterial Systematics. John Wiley & Sons, New York, N.Y.

10. Maidak, B. L., Larsen, V., McCaughey, M. J., Overbeck, R., Olsen, G. J., Fogel, K., Blandy, J. and Woese, C. R. (1994) The ribosomal database project. *Nucleic Acids Research* 22, 3485.
11. Norberg, A. B. and Molin, N. (1983) Toxicity of cadmium, cobalt, uranium and zinc to Zgogtoea ramigera. *Water Res.*, 17(10), 1333.
12. Paton, G. I., Palmer, G., Kindness, A., Campbell, C., Glover, L. A., and Killham, K. (1995) Use of luminescence-marked bacteria to assess copper bioavailability in malt whisky distillery effluent. *Chemosphere*, 31(5), 3217.
13. Stom, D. I., Geel, T. A., Balayan, A. E., Shachova, G. I., Kuznetsov, A. M., and Medvedeva, S. E. (1992) Bioluminescent method in studying the complex effect of sewage components. *Arch Envirom Contamt Toxicol.*, 22, 203.
14. Strotmann, U. J. and Eglsaer, H. (1995) The tonicit y of substituted phenols in the nitrification inhibition test and luminescent bacteria test. *Ecotoxicol. Environ. Saf.*, 30,269.
15. Volskay, V. T. Jr. and Grady, C. P. L. Jr. (1988) Toxicity of selected RCRA compounds to activated sludge microorganisms. *J. Water Pollut. Control Fed.*, 60(10), 1850.
16. Brock, T. D., D. W. Smith and M. T. Madigan (1974) *Biology of Microganisms*. Fourth Edition. Prentice-Hall, Inc., Englewood Clffs, N. J. T-847
17. Sambrook et al., *Molecular Cloning: A Laboratory Manal*, 2nd Ed., Cold Spring Harbor Laboratory, Cold Spring Harbor, N.Y., 1989
18. *Bergey's Manual of Systematic Bactetiology* (1984) Vol. 1–III, Eds. N. R. Krieg and J. G. Holt, Williams and Wilkins, Baltimore, Md.
19. *Manual on the Cases* and *Control of Activated Sludge Bulklng* and *Foaming* (1993) Lewis Publishers, Inc., Chelsea, Mich.

What is claimed is:

1. A method of making and using bioluminescent reporter bacteria, the method comprising the following steps:

a) obtaining bacteria from biological wastewater sludge of a wastewater treatment facility;

b) introducing into said bacteria a nucleic acid construct that encodes a bioluminescent reporter protein under conditions whereby the nucleic acid encoding the bioluminescent reporter protein is taken up by, and expressed in, said bacteria, and wherein the bioluminescent reporter protein does not naturally occur in said bacteria;

c) contacting the influent from the wastewater treatment facility with the bioluminescent reporter bacteria obtained by steps a) and b);

d) detecting the bioluminescent reporter protein expressed by the bioluminescent reporter bacteria; and e) correlating the presence of toxicity with the reduction in expression of the bioluminescent reporter protein;

wherein the bioluminescent reporter bacteria are made from bacteria obtained from the same wastewater treatment facility at which the bioluminescent reporter bacteria are to be used for detecting toxicity, and are therefore specifically adapted to the conditions of said wastewater treatment facility.

2. The method of claim 1, wherein the nucleic acid that encodes the reporter protein is a lux construct.

3. The method of claim 1, wherein the reporter protein is constitutively expressed.

4. The method of claim 1, wherein the introducing step is accomplished using a donor bacterium which contains the nucleic acid that encodes the bioluminescent reporter protein.

5. The method of claim 4, wherein the donor bacterium which contains the nucleic acid that encodes the bioluminescent reporter protein is *Escherichia coli*.

6. The method of claim 1, wherein the bacteria obtained from a biological wastewater sludge is selected from the group consisting of Zoogloea spp., Pseudomonas spp., Hyphomicrobium spp, Alcaligenes spp., Acinetobacter spp. and Sphaerotilus spp.

* * * * *